(12) United States Patent
Jerz

(10) Patent No.: US 6,700,014 B2
(45) Date of Patent: Mar. 2, 2004

(54) PROCESS FOR EXTRACTING OLEANOLIC ACID FROM PLANT MATERIAL

(75) Inventor: Gerold Jerz, Gruenwald (DE)

(73) Assignee: E. & J. Gallo Winery, Modesto, CA (US)

( * ) Notice: Subject to any disclaimer, the term of this patent is extended or adjusted under 35 U.S.C. 154(b) by 22 days.

(21) Appl. No.: 10/024,978

(22) Filed: Dec. 19, 2001

(65) Prior Publication Data

US 2003/0114708 A1 Jun. 19, 2003

(51) Int. Cl.[7] .............................................. C07C 61/12
(52) U.S. Cl. ...................................................... 562/498
(58) Field of Search ........................................ 562/498

(56) References Cited

U.S. PATENT DOCUMENTS

| 5,948,460 A | 9/1999 | Kang et al. |
| 6,037,492 A | 3/2000 | Lopez de Hierro |

FOREIGN PATENT DOCUMENTS

| EP | 0555484 A1 | 8/1993 |
| EP | 1013752 A1 | 6/2000 |
| WO | 9804331 | * 2/1998 |

OTHER PUBLICATIONS

Jing–Zhen Deng et al., "DNA Polymerase β Inhibitors from *Baeckea gunniana*," J. Natl. Prod. 1999, 62, 1624–1626.

M. Grncarevic et al., "A Review of the Surface Lipids of Grapes and Their Importance in the Drying Process," Am. J. Emol. Vitic. (22) 80–86, 1971.

Hye Gwang Jeong, "Inhibition of cytochrome P450 2E1 expression by oleanolic acid: hepatoprotective effects against carbon tetrachloride–induced hepatic injury," Toxicology Letters 105 (1999) 215–222.

Yoshiki Kashiwada et al., "Anti–AIDS Agents. 30. AntiHIV Activity of Oleanolic Acid, Pomolic Acid, and Structurally Related Triterpenoids," J. Nat. Prod. 1988, 61, 1090–1095.

Chaomei et al., "Inhibitory Effects of Constituents from *Cynomorium songaricum* and Related Triterpene Derivatives on HIV–1 Protease," Chem. Pharm. Bull. 47(2) 141–145 (1999).

Chao–Mei Ma et al., "Chemical Modification of Oleanene Type Triterpenes and Their Inhibitory Activity Against HIV–1 Protease Dimerization," Chem. Pharm. Bull, 48(11) 1681–1688 (2000).

F. Radley et al., "The Composition of Grape Cuticle Wax," Aust. J. Chem., 1965, 18, 1059–69.

F. Radler, "The Surface Waves of the Sultana Vine (*Vitis vinifera* cv. Thompson Seedless)," Aust. J. Biol. Sci., 1965, 18, 1045–1056.

\* cited by examiner

*Primary Examiner*—Paul J. Killos
(74) *Attorney, Agent, or Firm*—Marshall, Gerstein & Borun LLP

(57) ABSTRACT

A process for extracting oleanolic acid from plant material is disclosed. Dried plant material is provided and an extraction process is carried out with a non-halogenated polar to medium polar solvent. The resulting solution that contains oleanolic acid is separated from the plant material and the solvent is removed using cooling, vacuum-evaporation or other techniques. A precipitate is formed that contains mostly oleanolic acid. Subsequent purification steps to provide highly purified oleanolic acid include washing techniques, re-crystallization techniques or the use of chromatography.

47 Claims, No Drawings

PROCESS FOR EXTRACTING OLEANOLIC ACID FROM PLANT MATERIAL

TECHNICAL FIELD

The present invention relates generally to a process for extracting oleanolic acid. More specifically, the present invention relates to processes for extracting oleanolic acid from plant materials with non-halogenated, polar to medium polar solvents.

BACKGROUND

Oleanolic acid (3-β-hydroxyoleanan-12-en-28-oic acid) is a pentacyclic triterpene acid which is ubiquitously distributed throughout the plant kingdom. Oleanolic acid has a number of biological properties of interest. Specifically, oleanolic acid has been shown to have cytotoxicity against human tumor cell lines. Oleanolic acid is also known to have anti-fungal, anti-malarial, anti-carcinogenic, anti-inflammatory and anti-hepatotoxic activity. Further, oleanolic acid has also been shown to inhibit human topoisomerase I and II-α. Finally, oleanolic acid has also been known to inhibit HIV-1 protease.

Consequently, oleanolic acid is of increasing interest in pharmaceutical research circles because it may have distinct pharmaceutical properties of its own or provide a basis for the development of new pharmaceutical drugs by partial structure variation.

Because it is difficult to synthesize and extract from plant materials, oleanolic acid is expensive. Depending on the purity, oleanolic acid can cost from $300 to $400 per gram (purity grade approximately 97%) and up to $900 per gram (purity grade 99%). Accordingly, there is a need for an efficient method that will result in the obtaining of oleanolic acid in a pure form but at a low cost.

Oleanolic acid has been recovered for use of a food additive (i.e., in a non-pure form) from olive skins. In low concentration, it has also been applied in non-pure form to remove the metallic aftertaste sensation of artificial sweeteners.

Oleanolic acid has also been recovered in non-purified forms from grape skins in connection with the study of the wax that covers grape skins in order to enhance the drying rate of the grapes. Specifically, Radler and Horn, "The Composition of Grape Cuticle Wax," Aust. J. Chem., pp. 1059–69 (1965) teach the extraction of the grape skin wax with a light petroleum fraction. Radler and Horn disclose no process for the purification or isolation of oleanolic acid that may or may not be contained in the grape skin wax. However, a later article, Radler, "The Surface Waxes of Sultana Vine," Aust. J. Biol. Sci., pp. 1045–56 (1965) discloses the extraction of the surface waxes with chloroform. A similar extraction is also disclosed in Grncarevic and Radler, "A Review of Surface Lipids of Grapes and Their Importance in the Drying Process," Am. J. Enol. Vitic. (22), pp. 80–86 (1971).

The use of petroleum, similar solvents and chloroform in an extraction process for obtaining oleanolic acid from plant material is disadvantageous because chloroform is toxic, carcinogenic and dangerous to handle. Further, light petroleums, such as hexane, are not desirable because these very non-polar solvents do not selectively extract oleanolic acid but, instead, extract additional unwanted materials such as waxes, long-chain aldehydes and long-chain alcohols which are difficult to separate from the target compound oleanolic acid. Other non-polar solvents such as benzene, toluene, cyclohexane, and THF, are toxic and/or carcinogenic. Further, none of the above-described processes have been developed into a method for obtaining oleanolic acid from plant material in a relatively pure form.

Thus, due to the potential of oleanolic acid as a pharmaceutical agent and due to the high cost of oleanolic acid in a pure or relatively pure form, there is a need for an improved process for generating pure or relatively pure oleanolic acid in a more economical and safer fashion than current known processes.

SUMMARY OF THE DISCLOSURE

In satisfaction of the aforenoted needs, a process for extracting oleanolic acid from plant materials is disclosed. In the disclosed process, an initial extraction step is carried out with a non-halogenated polar to medium polar solvent. Specifically, plant material is provided which contains oleanolic acid. This plant material which is preferably dried, and, if applicable, seeds and stems are removed as the non-halogenated polar to medium polar solvent would extract seed oil as well as other semi-polar substances from the stems which would be difficult to separate from the oleanolic acid in the later processing steps. The extraction step with the non-halogenated polar to medium polar solvent results in a crude extract that comprises oleanolic acid.

The oleanolic acid is then removed from the solvent. Specifically, the oleanolic acid may then be crystallized out of the oversaturated solution to form a precipitate. The non-halogenated polar to medium polar solvent is removed from the precipitate by conventional means. Optionally, the precipitated oleanolic acid is then purified in different steps.

The oleanolic acid may be precipitated out of the solution by cooling the solution, adding an additional solvent such as water to the solution, or removing solvent by vacuum evaporation until the precipitate is formed.

The subsequent purification step can comprise dissolution of the precipitate in fresh non-halogenated polar to medium polar solvent and re-crystallization of the precipitate which will have a higher purity of oleanolic acid.

Subsequent re-crystallization can also involve dissolving the precipitate in fresh non-halogenated polar to medium polar solvent, adding controlled amounts of water until the oleanolic acid precipitates, separating the oleanolic acid precipitate from the resulting organic solvent/water solution resulting in increased purity of the oleanolic acid. Polar components such as tannins, phenolics and other impurities have a tendency to remain in the aqueous/organic solvent phase.

The subsequent purification can also comprise washing of the crystalline precipitate with small amounts of fresh solvent, washing the precipitate with a polar solvent or washing the precipitate with both a non-polar and a polar to medium polar solvent.

Preferably, for all steps including extraction and purification, the non-halogenated polar to medium polar solvent is ethanol due to its non-toxicity, abundance and low cost. Ethanol has a Snyder polarity index of 5.2. For purposes of this application, polar to medium polar solvents will be defined as those having a Snyder polarity index of greater than 2.5. On the other hand, non-polar solvents will hereinafter be defined as those non-polar solvents having a Snyder polarity index of less than 2.5. Other non-halogenated polar to medium polar solvents suitable for the initial extraction step and subsequent purification steps include (with the Snyder polarity index given in parenthesis)

e.g., isopropanol (4.3), n-propanol (4.3), methanol (6.6), diethylether (2.8), acetone (5.4), acetonitrile (6.2), methyl tertiary butyl ether (MTBE), and ethylacetate (4.3).

Non-halogenated solvents are preferred due to their general low cost, lower toxicity and ease of disposal.

If a non-polar solvent is used in the purification process, a suitable non-polar solvent one petroleum ether fractions ($C_5$–$C_7$), or n-hexane cyclohexane. Hexane has a Snyder polarity index of zero or close to zero.

Other suitable preparative purification steps include the use of column chromatography such as medium pressure liquid chromatography (MPLC) and preparative high performance liquid chromatography (HPLC).

Another purification step could include dissolving the oleanolic precipitate in a solvent and passing the resulting solution through one or more membranes.

One plant material which is abundant and relatively rich in oleanolic acid is grapes, grape pomace or still more specifically, grape skins. Accordingly, a suitable process according to this disclosure includes providing a material that comprises grape skins that has been either sun dried, air dried or freeze dried. Mixing a polar to medium polar solvent with the material, extracting a solution comprising the alcohol solvent and oleanolic acid from the material, cooling the solution to form a precipitate comprising oleanolic acid, removing the alcohol from the precipitate and, purifying the oleanolic acid and the precipitate using the processes described above. It will be also noted that the disclosed process is also suitable for use with olive pomace, almond hulls, medicinal plants and all other plant materials that include oleanolic acid which would be apparent to those skilled in the art.

Yet another disclosed process includes providing plant material, applying the supercritical fluid extraction technique (SFE) supercritical carbon dioxide gas, extracting the solution comprising the supercritical carbon dioxide and oleanolic acid from the plant material, removing the carbon dioxide from the solution to form an extraction-residue comprising the oleanolic acid and, subsequently purifying the oleanolic acid by changing the pressure or increasing the temperature to prompt a phase change of the carbon dioxide to a gas, which may then be released. In this process, the precipitate is relatively pure and the need for subsequent purification steps may be unnecessary or limited. In addition, the pressure of the supercritical $CO_2$ can be adjusted to change and/or control its extraction abilities. Further, it is contemplated that the extraction abilities of the supercritical $CO_2$ can be further modified by the incorporation of polar modifiers such as methanol or ethanol.

DETAILED DESCRIPTION OF THE PRESENTLY PREFERRED EMBODIMENTS

While olive skins, almond hulls and other plant materials are known to contain oleanolic acid, the disclosed process will be described in detail in connection with the use of grape pomace or a material that includes grape skins. Grape pomace and grape skins are an abundant material as it is a residual product from the wine making and grape juice industries. Removal of the oleanolic acid from material still renders the material useful as animal feed or other agricultural uses as the disclosed process avoids the use of toxic solvents. Further, by avoiding the use of toxic solvents, the process is safer and also more efficient. The disclosed process also avoids the use of extremely flammable, explosive solvents such as hexane.

Grape pomace or a material that includes grape skins is initially provided and, if not already dried, can be dried using conventional techniques, including freeze drying, sun and air drying or the application of mild heat. Oleanolic acid is relatively heat stable and the recovery rate will not be substantially affected by the drying process. The material needs not to be fresh, and may also be several months old without any change or loss of oleanolic acid. Seeds and stems are removed from the dried material using a so-called air knife or other suitable process. Removal of the seeds is important as the seeds include oils which are difficult to separate from the recovered oleanolic acid. Stems as well should be removed as far as possible, because they contain amounts of exchangeable chlorophylls, tannins and hydrocarbons.

An initial extraction step is carried out with a non-halogenated polar to medium polar solvent. The preferred solvent is ethanol, because it is abundant and relatively inexpensive. The material is mixed with the non-halogenated polar to medium polar solvent to yield a solution containing oleanolic acid. The solution is separated from the material by filtration and subsequently cooled to form a precipitate. Other means for causing the precipitate to form such as adding a second solvent or vacuum evaporation will be apparent to those skilled in the art. The remaining solution, which comprises solvents and impurities such as tannins, triterpenes and other polyphenolics, as well as other impurities, is removed leaving a crystallized precipitate that comprises mostly oleanolic acid. The solvent may be removed using vacuum-evaporation, centrifuging or other techniques. The resulting precipitate has an oleanolic acid purity ranging from about 70% to about 80%. The remaining materials are typically poly-phenols, e.g., oligomeric and polymeric tannins.

The subsequent purification steps can include re-crystallization with fresh non-halogenated polar to medium polar solvent. Again, ethanol is the preferred solvent but other solvents may include isopropanol, methanol, n-propanol, methyl-t-butyl ether, diethylether, petrolether and tetrahydrofuran. The second precipitate is formed by removing excess solvent by vacuum-evaporation or a simple cooling of the solution to reprecipitate the oleanolic acid and removing the remaining solvent by conventional means.

Yet another purification process can include dissolving the initial precipitate with fresh non-halogenated polar to medium polar solvents, such as ethanol. Adding controlled amounts of water, or another medium polar solvent will reprecipitate oleanolic acid which went into solution. The water/organic solvent mixture is removed by centrifugation, vacuum-evaporation or other conventional means.

Other purification processes can include washing of the precipitate with fresh non-halogenated polar to medium polar solvent, washing the precipitate with polar solvent, such as ethanol or a combination of washing steps including the use of non-halogenated polar to medium polar solvent and a polar solvent. Preferably, the last washing step should be performed with a non-halogenated polar to medium polar solvent.

Still other preparative purification techniques include the use of chromatography, such as thin layer chromatography, medium pressure liquid chromatography (MPLC) and preparative high performance liquid chromatography (HPLC). Known chromatography techniques include the use of silicon dioxide support material and a dichloromethane/methanol mixture as a solvent-system or reversed phase-material, preferably, octadecylsilene (C18) applying methanol as a recoverable solvent.

Also, the oleanolic acid precipitate could be dissolved in a solvent and the resulting solution passed through one or more membranes.

Yet another extraction technique involves the use of supercritical carbon dioxide, which has a polarity similar to hexane. Such a supercritical fluid extraction technique (SFE) involves the extraction of the plant material, e.g., grape pomace or grape skins, with pressurized ("fluid") carbon dioxide. After evaporation of $CO_2$, oleanolic acid is recovered. This results in a high purity oleanolic acid which may, if necessary, be purified further using the purification steps described above.

As a result, the disadvantages of using non-polar (very lipophilic) solvents, e.g., hexane, or toxic solvents, e.g., chloroform or dichloromethane, taught by the prior art are avoided. Surprisingly, oleanolic acid, which polarity character is amphiphilic due to an acidic and hydroxyl functional group, has been previously extracted within non-polar solvents, can as well be extracted with a polar to medium polar solvent, of which many non-halogenated choices are available. Accordingly, an inexpensive and abundant non-halogenated polar to medium solvent is ethanol. However, other suitable non-halogenated polar to medium polar solvents are available, known to those skilled in the art, and may prove to be useful in preparing oleanolic acid in a highly purified state.

It should be understood that the extraction and purification steps described above are mere examples and are not intended to be limiting of the disclosure. In certain instances, details which are not necessary for an understanding of the disclosed processes or which render other details difficult to perceive may have been omitted. It should be understood, of course, that the disclosed processes are not necessarily limited to the particular embodiments illustrated herein.

What is claimed:

1. A process for extracting oleanolic acid from plant material comprising:
   providing plant material that comprises oleanolic acid;
   mixing a non-halogenated polar to medium polar solvent with the plant material; and
   extracting a solution comprising the non-halogenated polar to medium polar solvent and oleanolic acid from the plant material.

2. The process of claim 1 further comprising:
   forming a precipitate comprising the oleanolic acid from the solution; and
   removing the non-halogenated polar to medium polar solvent from the precipitate.

3. The process of claim 2 further comprising;
   purifying the oleanolic acid in the precipitate.

4. The process of claim 2 wherein the step of forming the precipitate comprises cooling the solution.

5. The process of claim 2 wherein the step of forming the precipitate comprises adding a secondary solvent to the solution.

6. The process of claim 5 wherein the secondary solvent is water.

7. The process of claim 2 wherein the step of forming the precipitate comprises vacuum evaporating the solution.

8. The process of claim 3 wherein the purifying step comprises washing the precipitate with small amounts of a non-polar solvent.

9. The process of claim 3 wherein the purifying step comprises washing the precipitate with a second non-halogenated polar to medium polar solvent.

10. The process of claim 3 wherein the purifying step comprises washing the precipitate with a non-polar solvent and a polar to medium polar solvent.

11. The process of claim 1 wherein the non-halogenated polar to medium polar solvent is selected from the group consisting of ethanol, isopropanol, n-propanol, methanol, acetone methyl-t-butyl ether, diethylether and tetrahydrofuran, acetonitrile, ethylacetate and mixtures thereof.

12. The process of claim 8 wherein the non-polar solvent is n-hexane and petrolether fractions ($C_5$–$C_7$), cyclohexane.

13. The process of claim 9 wherein the second non-halogenated polar to medium polar solvent is selected from the group consisting of ethanol, isopropanol, n-propanol, methanol, n-butanol, acetone ethylacetate and mixtures thereof.

14. The process of claim 1 wherein the plant material is freeze dried, sun dried or thermally dried.

15. The process of claim 3 wherein the purifying step comprises chromatography.

16. The process of claim 15 wherein the chromatography is medium pressure liquid chromatography (MPLC).

17. The process of claim 15 wherein the chromatography is high performance liquid chromatography (HPLC).

18. The process of claim 3 wherein the purifying step comprises forming a second solution by dissolving the precipitate in a second polar to medium polar solvent, cooling the second solution to provide a second precipitate comprising oleanolic acid and removing the second polar to medium polar solvent from the second precipitate.

19. The process of claim 18 wherein the second polar to medium polar solvent is selected from the group consisting of ethanol, isopropanol, n-propanol, methanol, n-butanol, acetonitrile, MTBE, acetone, ethylacetate and mixtures thereof.

20. The process of claim 3 wherein the purifying step comprises forming a second solution by dissolving the precipitate in a second polar to medium polar solvent, adding water to the second solution until a second precipitate appears, centrifuging the water, second polar to medium polar solvent and second precipitate and removing the water and second polar to medium polar solvent from the second precipitate.

21. The process of claim 20 wherein the second polar to medium polar solvent is selected from the group consisting of ethanol, n-propanol, isopropanol, methanol, n-butanol, acetone, MTBE, acetonitrile, ethylacetate and mixtures thereof.

22. The process of claim 3 wherein the purification process comprises dissolving the precipitate in a solvent to form a solution and passing the solution through at least one membrane.

23. The process of claim 22 wherein the membrane is an ultrafultuation membrane selected to retain tannins and polyphenolics but not oleanolic acid.

24. The process of claim 1 wherein the plant material is derived from grapes.

25. The process of claim 1 further comprising removing seeds and stems from the plant material before mixing the plant material with the non-halogenated polar to medium polar solvent.

26. A process for extracting oleanolic acid from a material that comprises grape skins, the process comprising:
   providing dry material;
   mixing an alcohol and another polar or medium polar non-halogenated solvent with the material;
   extracting a solution comprising the alcohol, the other polar to medium polar solvent and oleanolic acid from the material;
   forming a precipitate comprising oleanolic acid from the solution;
   removing the alcohol and the other polar to medium polar solvent from the precipitate; and
   purifying the oleanolic acid in the precipitate.

27. The process of claim 26 wherein the step of forming the precipitate comprises cooling the solution.

28. The process of claim 26 wherein the step of forming the precipitate comprises adding a secondary solvent to the solution.

29. The process of claim 26 wherein the secondary solvent is water.

30. The process of claim 26 wherein the step of forming the precipitate comprises vacuum evaporating the solution.

31. The process of claim 26 wherein the purifying comprises washing the precipitate with a second polar to medium polar solvent.

32. The process of claim 26 wherein the alcohol solvent or other polar to medium polar solvent is selected from the group consisting of ethanol, isopropanol, n-propanol, methanol, n-butanol, acetone, ethylacetate, acetonitrile, MTBE and mixtures thereof.

33. The process of claim 31 wherein the second polar to medium polar solvent is selected from the group consisting of ethanol, isopropanol, n-propanol, methanol, n-butanol, acetone, ethylacetate, acetonitrile, MTBE and mixtures thereof.

34. The process of claim 25 wherein the purifying step comprises chromatography.

35. The process of claim 34 wherein the chromatography is medium pressure liquid chromatography (MPLC).

36. The process of claim 34 wherein the chromatography is high performance liquid chromatography (HPLC).

37. The process of claim 26 wherein the purifying step comprises forming a second solution by dissolving the precipitate in a second polar to medium polar solvent, cooling the second solution to provide a second precipitate comprising oleanolic acid and removing the second polar to medium polar solvent from the second precipitate.

38. The process of claim 37 wherein the second polar to medium polar solvent is selected from the group consisting of ethanol, isopropanol, n-propanol, methanol, n-butanol, acetone, ethylacetate, MTBE and mixtures thereof.

39. The process of claim 26 wherein the purifying step comprises forming a second solution by dissolving the precipitate in a second polar to medium polar solvent, adding water to the second solution until a second precipitate appears, centrifuging the water, second polar to medium polar solvent and second precipitate and removing the water and second polar to medium polar solvent from the second precipitate.

40. The process of claim 26 wherein the second polar to medium polar solvent is selected from the group consisting of ethanol, isopropanol, n-propanol, methanol, n-butanol, acetone, ethylacetate and mixtures thereof.

41. The process of claim 26 wherein the material is grape pomace.

42. A process for extracting oleanolic acid from plant material comprising:

providing plant material;

mixing supercritical carbon dioxide with the plant material;

recovering an extract comprising the supercritical carbon dioxide and oleanolic acid from the plant material;

removing the carbon dioxide from the solution to form a precipitate comprising the oleanolic acid;

purifying the oleanolic acid in the precipitate.

43. The process of claim 42 wherein the purifying step comprises washing the precipitate with a solvent.

44. The process of claim 42 wherein the material comprises grape skins.

45. Oleanolic acid separated from grape pomace in accordance with the process of claim 1.

46. Oleanolic acid separated from grape pomace in accordance with the process of claim 26.

47. Oleanolic acid separated from grape pomace in accordance with the process of claim 42.

* * * * *